United States Patent [19]
de Rigal et al.

[11] Patent Number: 5,618,521
[45] Date of Patent: Apr. 8, 1997

[54] PHOTOPROTECTIVE/COSMETIC COMPOSITIONS COMPRISING ANTIOXIDANTS AND FILAMENTOUS BACTERIAL EXTRACTS

[75] Inventors: Jean de Rigal, Claye Souilly; Jean-Luc Leveque, Le Raincy; Jean-Claude Contamin, Cantaron; Lucien Aubert, Cap d'Ail, all of France

[73] Assignee: L'Oreal, Paris, France

[21] Appl. No.: 491,454

[22] Filed: Jun. 16, 1995

[30] Foreign Application Priority Data

Jun. 16, 1994 [FR] France .................................. 94 07397

[51] Int. Cl.$^6$ .............................. A61K 7/42; A61K 35/74
[52] U.S. Cl. ..................... 424/59; 424/195.1; 435/822; 514/783
[58] Field of Search .................... 424/59, 195.1; 435/822; 514/783

[56] References Cited

FOREIGN PATENT DOCUMENTS

| 2283223 | 3/1976 | France . |
|---|---|---|
| 2693654 | 1/1994 | France . |
| 2034687 | 6/1980 | United Kingdom . |

*Primary Examiner*—Shelley A. Dodson
*Attorney, Agent, or Firm*—Burns, Doane, Swecker & Mathis, L.L.P.

[57] ABSTRACT

Topically applicable sunscreen/cosmetic compositions well suited for enhanced photoprotection of human skin and/or hair against the damaging effects of UV-A and UV-B irradiation, whether before, during and/or after exposure to such UV irradiation, particularly solar radiation, comprise a photoprotecting effective amount of (i) at least one antioxidant, for example tocopherol or derivative thereof, and (ii) at least one extract of at least one nonphotosynthetic and nonfructifying filamentous bacteria, for example of the order Beggiatoales, in a cosmetically acceptable vehicle, diluent or carrier therefor.

17 Claims, No Drawings

PHOTOPROTECTIVE/COSMETIC COMPOSITIONS COMPRISING ANTIOXIDANTS AND FILAMENTOUS BACTERIAL EXTRACTS

BACKGROUND OF THE INVENTION

1. Technical Field of the Invention

The present invention relates to novel cosmetic or pharmaceutical compositions for topical application, for the photoprotection of the skin and/or the hair, whether before, during and/or after exposure to UV radiation, and to the use of same for preventing and/or attenuating the damage caused by such UV irradiation.

This invention more especially relates to the aforesaid photoprotective/cosmetic compositions comprising, in a cosmetically acceptable vehicle, carrier or diluent therefor, combinatory immixture of at least one antioxidant and at least one extract of at least one judiciously selected filamentous bacterium.

2. Description of the Prior Art

It is known to this art that light radiation of wavelengths of from 320 nm to 400 nm (UV-A) promotes tanning of the human epidermis; such radiation, however, is likely to cause damage to the skin, especially in the case of sensitive skin or skin which is continuously exposed to solar radiation. UV-A rays cause, in particular, a loss in the elasticity of the skin and the appearance of wrinkles, promoting a premature aging thereof.

It is also known to this art that light rays having wavelengths of from 280 to 320 nm (UV-B) cause erythema and skin burning which can impair the natural development of a tan.

It is thus necessary, in order to maintain suitable skin quality after exposure to UV radiation, to prepare or treat the skin before the exposure, to protect it during the exposure and even to attenuate the damage caused by the exposure.

SUMMARY OF THE INVENTION

Accordingly, a major object of the present invention is the provision of novel photoprotective/cosmetic compositions for topical application to the skin and/or the hair, before, during and/or after exposure to UV radiation and which prevent and/or attenuate the damage or deleterious effects caused by said radiation.

Briefly, the present invention features novel photoprotective/cosmetic compositions for topical application, for the photoprotection of the skin and/or the hair, comprising, in a cosmetically acceptable vehicle, diluent or carrier, an effective amount of (i) at least one antioxidant and (ii) at least one extract of at least one nonphotosynthetic and nonfructifying filamentous bacteria.

DETAILED DESCRIPTION OF BEST MODE AND PREFERRED EMBODIMENTS OF THE INVENTION

More particularly according to the present invention, the subject compositions comprise, as the active agents therefor, combinatory immixture of at least one antioxidant and at least one extract of at least one nonphotosynthetic and nonfructifying filamentous bacteria.

Indeed, it has now surprisingly and unexpectedly been determined that admixture of these two very specific constituents elicits an enhanced effect or response in respect of the photoprotection of human skin and/or hair.

By the term "extract of nonphotosynthetic and nonfructifying filamentous bacteria" are intended both the actual extracts and the biomass obtained after culturing said bacteria, such biomass optionally being partially dehydrated and/or ground.

The bacterial extracts according to the invention are prepared from nonphotosynthetic and nonfructifying filamentous bacteria as defined per the classification of Bergey's *Manual of Systematic Bacteriology* (vol. 3, section 23, 9th edition, 1989). Representative thereof are the bacteria belonging to the order of Beggiatoales, and more particularly the bacteria of the genera Beggiatoa, Vitreoscilla, Flexithrix or Leucothrix. Among the bacteria of the genus Beggiatoa, the bacteria of strains of Beggiatoa alba (ATCC 33555) are the preferred.

To prepare the extract according to the invention, the bacteria may be cultured according to any one of a number of techniques known to this art, and subsequently separated from the biomass obtained, for example by filtration, centrifugation and/or freezedrying.

The extract may be employed in the form of derivatives thereof, for example in the form of at least partially acylated derivatives. The acylation may then be carried out using an organic carboxylic anhydride, such as acetic anhydride, or using the corresponding acid chloride, such as acetyl chloride. The acylation is carried out such that at least some of the primary and secondary amine functional groups present in the bacterial biomass are acylated.

The compositions according to the invention advantageously have a 0.01% to 2% solids content of bacterial extract relative to the total weight of the composition.

The bacterial extract may be incorporated in dispersion form in a suitable vehicle such as water, organic solvents and fatty substances including oils, whether alone or in admixture.

The cosmetic compositions according to the invention also comprise an antioxidant. By the term "antioxidant" is intended any compound or agent exhibiting activity against oxygenated free radicals and/or peroxide-inactivating activity.

Such antioxidants are typically present in the subject compositions in an amount ranging from 0.001% to 30% by weight, said amount depending on the nature and activity of the particular antioxidant.

Exemplary of such antioxidants are:

(1) Tocopherol and derivatives thereof, for example the acetate, linoleate or nicotinate, preferably at concentrations on the order of 0.1% to 5%;

(2) γ-Orizanol (0.1% to 5%);

(3) Lysine pidolate or arginine pidolate (0.5% to 10%);

(4) Plant extracts such as extract of balm (0.01% to 2%), extract of silimarin (0.01% to 2%), extract of gingko (0.05% to 2%), extract of sage (0.05% to 2%), extract of cola nuts (0.05% to 2%), extract of rutin (0.1% to 2%), or extract of thyme (0.1% to 2%), the % symbol representing the solids content;

(5) Proanthocyanolidine oligomers of pine, of hawthorn or of grape (0.1% to 2%);

(6) Di-tert-butylhydroxybenzylidenecamphor (0.1% to 2%);

(7) Green tea (0.1% to 2%);
(8) Caffeine (0.1% to 5%);
(9) Glycerol (2% to 30%);
(10) Mannitol (2% to 30%);
(11) Carnosine (0.1% to 2%);
(12) Superoxide dismutase (100 to 10,000 IU/100 g);
(13) Guanosine (0.01% to 1%);
(14) Microalgae containing ethoxyquine, such as Hematococcus (0.005% to 1%);
(15) Pentasodium aminotrimethylenephosphonate (0.001% to 0.5%);
(16) Lactoperoxidase (0.01% to 0.1%); and
(17) Lactoferrin (0.01% to 0.1%).

A mixture of a plurality of antioxidants may also be used.

The compositions according to the invention may be presented in all of the forms which are conventional or known in the cosmetic and/or pharmaceutical arts, in the form of a skincare product, a sunscreen product, a post-solar exposure or sunburn product, a hair product, or a makeup product.

The compositions according to the invention may thus additionally comprise at least one conventional photoprotective agent suitable for screening UV (UV-A and/or UV-B) irradiation, for example one or more organic sunscreens (UV absorbing agents) and/or one or more inorganic (nano)pigments based on metal oxides, and in particular based on titanium dioxide, which functions by physically blocking the radiation (UV reflectors and/or diffusers).

Such conventional organic sunscreens may be selected, whether alone or in admixture, from among 2-phenylbenzimidazole-5-sulfonic acid and salts thereof, cinnamic derivatives such as 2-ethylhexyl p-methoxycinnamate, salicylic derivatives such as 2-ethylhexyl salicylate and homomenthyl salicylate, camphor derivatives such as, for example, 3-(4-methylbenzylidene)camphor or (1,4-divinylbenzene)camphorsulfonic acid and derivatives thereof (FR-2,528,420), triazine derivatives such as 2,4,6-tris[p-(2'-ethylhexyl-1'-oxycarbonyl)anilino]-1,3,5-triazine, benzophenone derivatives such as 2-hydroxy-4-methoxybenzophenone, dibenzoylmethane derivatives such as 4-tert-butyl-4'-methoxydibenzoylmethane, ββ-diphenylacrylate derivatives such as 2-ethylhexyl α-cyano-ββ-diphenylacrylate, p-aminobenzoic acid derivatives such as octyl paradimethylaminobenzoate, menthyl anthranilate, and the sunscreen polymers and sunscreen silicones described in WO-93/04,665. Other examples of organic sunscreen agents are described in EP-A-0,487,404.

The organic sunscreen agent or agents are advantageously present in the compositions according to the invention at a concentration ranging from 0.1% to 30% by weight, and preferably from 0.5% to 25% by weight, relative to the total weight of the composition.

The metal oxides constituting pigments or nanopigments which are suitable for formulation into the compositions of the present invention include those already per se known to this art for their photoprotective activity. Thus, they may be selected from among, in particular, and whether alone or in admixture, titanium dioxide, zinc oxide, iron oxide, zirconium oxide, cerium oxide, or mixtures thereof.

Metal oxide nanopigments are the preferred.

Such metal oxide nanopigments, whether or not coated, are materials known to this art and are described, in particular, in EP-A-0,518,773, hereby expressly incorporated by reference. Additional and commercially available nanopigments not described therein, but which are also suitable according to this invention, include the products marketed under the trademarks UVT M 160, UVT M 212 and UVT M 262 by Kemira, and MT 100 SA or MT 100 SAS by Tayca.

The average size of the primary particles of the nanopigments present in the compositions according to the invention generally ranges from 5 nm to 100 nm, preferably from 10 to 40 nm.

The nanopigments are advantageously present in the compositions according to the invention at a concentration ranging from 0.1% to 30% by weight, and preferably from 1% to 20% by weight, relative to the total weight of the composition.

The overall content of the (organic sunscreen compound(s)+(nano)pigment(s)) photoprotective immixture preferably does not exceed 40% of the total weight of the final sunscreen composition.

The compositions according to the invention may additionally comprise other sunscreen agents such as, for example, those described in FR-2,528,420 and preferably the triethanolamine salt of terephthalylidene dicamphorsulfonic acid or MEXORYL SX®.

The compositions of this invention may be in the form of a simple or complex (O/W, W/O, O/W/O or W/O/W) emulsion such as a cream, a milk, a gel, an ointment or a cream-gel, in the form of a powder or a solid stick, or, alternatively, in the form of a liquid, optionally packaged as an aerosol, and may be provided in the form of a foam or a spray. They may also be formulated as a suspension or a dispersion in solvents or fatty matrices, in the form of a nonionic vesicle dispersion, in the form of a shampoo, lotion or a hair fixing spray, or, alternatively, in anhydrous or aqueous, solid or pasty form.

The compositions of the invention may be formulated according to any one of a number of techniques that are well known to this art.

In order to further illustrate the present invention and the advantages thereof, the following specific examples are given, it being understood that same are intended only as illustrative and in nowise limitative.

In said examples to follow, as in the above description, all parts and percentages are given by weight, unless otherwise indicated.

EXAMPLE 1

A photoprotective composition having the following composition was formulated:

| | |
|---|---|
| (a) Stearic acid | 3.0% |
| (b) Cetyl alcohol | 2.0% |
| (c) Self-emulsifiable glyceryl monostearate | 2.5% |
| (d) Petrolatum | 2.0% |
| (e) Sunflower oil | 6.0% |
| (f) Perhydrosqualene | 3.0% |
| (g) Octyl methoxycinnamate | 4.0% |
| (h) Triethanolamine salt of terephthalylidene dicamphorsulfonic acid (MEXORYL SX) | 2.6% |
| (i) Glycerol | 3.0% |
| (j) Preservatives | 0.3% |
| (k) Superoxide dismutase | 1,200 IU/100 g |
| (l) Pentasodium aminotrimethylenephosphonate | 0.1% |
| (m) Tocopherol | 2.0% |
| (n) Extract of *Beggiatoa alba* bacteria | 0.05% |
| (o) Water | qs 100% |

A composition which provides good photoprotection for the skin against UV radiation is thus obtained.

EXAMPLE 2

A post-solar exposure composition having the following composition was formulated:

| | | |
|---|---|---|
| (a) Cetostearyl alcohol | | 1.0% |
| (b) Cetyl alcohol | | 2.0% |
| (c) Self-emulsifiable glyceryl monostearate | | 3.0% |
| (d) Karite butter | | 3.0% |
| (e) Rice bran oil | | 1.0% |
| (f) Avocado oil | | 2.0% |
| (g) Dioctyl palmitate | | 5.0% |
| (h) Preservatives | | 0.3% |
| (i) Cyclomethicone | | 1.0% |
| (j) Carbomer 940 | | 0.3% |
| (k) Triethanolamine | | 0.3% |
| (l) Tocopherol acetate | | 3.0% |
| (m) Extract of *Beggiatoa alba* bacteria | | 0.1% |
| (n) Water | qs | 100% |

A post-solar exposure composition suitable for attenuating the damage caused by UV radiation is thus obtained.

EXAMPLE 3

A skincare cream having the following composition was formulated:

| | | |
|---|---|---|
| (a) Stearic acid | | 3.0% |
| (b) Cetyl alcohol | | 2.0% |
| (c) Self-emulsifiable glyceryl monostearate | | 3.0% |
| (d) Octyl methoxycinnamate | | 2.0% |
| (e) Glycerol | | 5.0% |
| (f) Preservatives | | 0.3% |
| (g) Superoxide dismutase | | 1,000 IU/100 g |
| (h) Tocopherol | | 2.0% |
| (i) Extract of *Beggiatoa alba* bacteria | | 0.05% |
| (j) Carbomer 940 | | 0.2% |
| (k) Triethanolamine | | 0.2% |
| (l) Water | qs | 100% |

A composition which provides good skin photoprotection is thus obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable sunscreen/cosmetic composition adopted for the photoprotection of human skin and/or hair, comprising a photoprotecting effective amount of (i) at least one antioxidant and (ii) at least one extract of at least one nonphotosynthetic and nonfructifying filamentous bacteria, in a cosmetically acceptable vehicle, diluent or carrier therefor.

2. The sunscreen/cosmetic composition as defined by claim 1, said at least one filamentous bacteria belonging to the order of Beggiatoales.

3. The sunscreen/cosmetic composition as defined by claim 2, said at least one filamentous bacteria being of the genera Beggiatoa, Vitreoscilla, Flexithrix or Leucothrix.

4. The sunscreen/cosmetic composition as defined by claim 3, said at least one bacteria being of the strain *Beggiatoa alba*.

5. The sunscreen/cosmetic composition as defined by claim 1, said at least one antioxidant comprising tocopherol or derivative thereof, γ-orizanol, lysine pidolate or arginine pidolate, an extract of balm, of silimarin, of gingko, of sage, of cola nuts, of rutin or of thyme, a proanthocyanolidine oligomer of pine, of hawthorn or of grape, di-tert-butylhydroxybenzylidenecamphor, green tea, caffeine, glycerol, mannitol, carnosine, superoxide dismutase, guanosine, microalgae containing ethoxyquine, pentasodium aminotrimethylenephosphonate, lactoperoxidase, lactoferrin, or mixture thereof.

6. The sunscreen/cosmetic composition as defined by claim 1, comprising from 0.001% to 30% by weight of said at least one antioxidant, relative to the total weight thereof.

7. The sunscreen/cosmetic composition as defined by claim 6, comprising from 0.01% to 2% by weight at said at least one bacterial extract, relative to the total weight thereof.

8. The sunscreen/cosmetic composition as defined by claim 1, comprising at least one other organic or inorganic UV-A and/or UV-B sunscreen.

9. The sunscreen/cosmetic composition as defined by claim 8, said at least one other sunscreen comprising particulates of an inorganic (nano)pigment based on a metal oxide.

10. The sunscreen/cosmetic composition as defined by claim 8, said at least one other sunscreen comprising at least one 2-phenylbenzimidazole-5-sulfonic acid or salt thereof, cinnamic derivative, salicylic derivative, camphor derivative, triazine derivative, benzophenone derivative, dibenzoylmethane derivative, β,β-diphenylacrylate derivative, p-aminobenzoic acid derivative, sunscreen polymer, or sunscreen silicone.

11. The sunscreen/cosmetic composition as defined by claim 8, said at least one other sunscreen comprising the triethanolamine salt of terephthalylidene dicamphorsulfonic acid.

12. The sunscreen/cosmetic composition as defined by claim 1, comprising an oil-in-water emulsion.

13. The sunscreen/cosmetic composition as defined by claim 1, comprising a water-in-oil emulsion.

14. The sunscreen/cosmetic composition as defined by claim 1, comprising a cream, milk, gel, lotion, ointment, cream-gel, suspension, dispersion, solid, paste, powder, foam, or spray.

15. The sunscreen/cosmetic composition as defined by claim 14, comprising a makeup, aerosol, shampoo, or hair spray.

16. A method for protecting human skin and/or hair against the deleterious effects of ultraviolet irradiation, comprising topically applying thereto, whether before, during and/or after exposure to such irradiation, an effective amount of the sunscreen/cosmetic composition as defined by claim 1.

17. A method for protecting human skin and/or hair against the deleterious effects of solar radiation, comprising topically applying thereto, whether before, during and/or after exposure to such radiation, an effective amount of the sunscreen/cosmetic composition as defined by claim 1.

* * * * *